United States Patent [19]

Wassen et al.

[11] 4,081,442

[45] Mar. 28, 1978

[54] PROCESS FOR THE RECOVERY OF ε-CAPROLACTAM FROM A REACTION MIXTURE OF ε-CAPROLACTAM AND SULPHURIC ACID

[75] Inventors: Willem J. Wassen, Geleen; Reijer Goettsch, Beek (L), both of Netherlands

[73] Assignee: Stamicarbon, B.V., Geleen, Netherlands

[21] Appl. No.: 765,102

[22] Filed: Feb. 2, 1977

[30] Foreign Application Priority Data

Feb. 3, 1976 Netherlands .......................... 7601061

[51] Int. Cl.$^2$ .................. C07D 201/16; C07D 201/04
[52] U.S. Cl. .............................. 260/239.3 A; 423/356; 423/541 R; 423/541 A; 423/544; 423/550; 423/549
[58] Field of Search ................................. 260/239.3 A

[56] References Cited

U.S. PATENT DOCUMENTS

| | | | |
|---|---|---|---|
| 2,723,266 | 11/1955 | Lincoln et al. | 260/239.3 A |
| 3,264,060 | 8/1966 | Nieswandt et al. | 260/239.3 A |
| 3,275,407 | 9/1966 | Furkert et al. | 423/356 |
| 3,364,202 | 1/1968 | De Rooij et al. | 260/239.3 A |
| 3,725,391 | 4/1973 | Suzuki et al. | 260/239.3 A |
| 3,801,566 | 4/1974 | Elmendorp et al. | 260/239.3 A |
| 3,810,968 | 5/1974 | Renault et al. | 423/356 |
| 3,850,910 | 11/1974 | Goettsch et al. | 260/239.3 A |
| 3,852,273 | 12/1974 | De Rooij | 260/239.3 A |
| 3,859,278 | 1/1975 | De Rooij et al. | 260/239.3 A |
| 3,991,047 | 11/1976 | Moudry et al. | 260/239.3 A |

FOREIGN PATENT DOCUMENTS 1,014,945  12/1965  United Kingdom ................. 423/356

*Primary Examiner*—Henry R. Jiles
*Assistant Examiner*—Robert T. Bond
*Attorney, Agent, or Firm*—Cushman, Darby & Cushman

[57] ABSTRACT

A process for removing sulfuric acid from reaction mixtures containing sulfuric acid and ε-caprolactam by treating the sulfuric acid with ammonia and sulfur dioxide to produce ammonium sulfate salts and reducing the ammonium sulfate salts to ammonia and sulfur dioxide.

4 Claims, 2 Drawing Figures

4,081,442

PROCESS FOR THE RECOVERY OF ε-CAPROLACTAM FROM A REACTION MIXTURE OF ε-CAPROLACTAM AND SULPHURIC ACID

BACKGROUND OF THE INVENTION

The invention relates to a process for the recovery of ε-caprolactam from a reaction mixture of ε-caprolactam and sulfuric acid in which all or part of the sulfuric acid is bound as ammonium salt to form an aqueous solution or a melt containing said sulfuric acid bound as ammonium salt.

A reaction mixture of this type is produced, for instance, in the Beckmann rearrangement of cyclohexanone oxime, to produce ε-caprolactam, by treating that oxime with sulfuric acid, oleum, or sulfur trioxide, and in the preparation of ε-caprolactam by reacting cyclohexane carboxylic acid with a nitrosating agent in the presence of sulfuric acid.

The lactam can be recovered from the reaction mixture of lactam and sulfuric acid by conventional methods. For instance, U.S. Pat. No. 2,993,889 shows such a recovery by neutralizing the sulfuric acid in the reaction mixture with ammonia water to form ammonium sulfate, after which the resulting ammonium sulfate can be separated from the lactam. A disadvantage of this method is that a large amount of ammonium sulfate results as a by-product which does not always find a ready market.

U.S. Pat. No. 3,336,298 overcomes this disadvantage by replacing the ammonia water for the neutralization of the sulfuric acid in the reaction mixture to form ammonium sulfate, by ammonium sulfate. Use of ammonium sulfate to neutralize the sulfuric acid in said reaction mixtures results in production of ammonium hydrogen sulfate as a by-product, instead of ammonium sulfate; and then the lactam is separated from the ammonium hydrogen sulfate by extraction. After extraction of the lactam a concentrated aqueous solution of ammonium hydrogen sulfate will remain which can be used, e.g., in the decomposition of phosphate rock. In a process of this type no ammonium sulfate is obtained as a by-product; however, the recovery of the lactam is then bound up with the preparation of another product.

The prior art is aware of a process for recovering lactam without the formation of by-products. In U.S. Pat. No. 3,852,272 part of the sulfuric acid is neutralized with ammonia water; and, after extraction of the lactam from the partly neutralized mixture, an aqueous solution containing ammonium hydrogen sulfate remains that is burned to form sulfur dioxide which can be converted to sulfuric aicd, (which is required for the formation of the reaction mixture of lactam and sulfuric acid). A disadvantage of this method is the loss of ammonia in the combustion of the ammonium hydrogen sulfate, as the ammonia in the ammonium hydrogen sulfate is converted completely to nitrogen and water.

In U.S. Pat. No. 3,879,380 a process is disclosed for the recovery of the lactam without the formation of by-products and without combustion of ammonia. In this process part of the sulphuric acid is neutralized with formation of an ammonium hydrogen sulphate melt and in which ammonia and sulphur trioxide are revovered from this melt with the aid of a suitable metal oxide for instance zinc oxide. Such a recovery of ammonia and sulphur trioxide is very expensive.

DESCRIPTION OF THE INVENTION

The invention provides a simple process which allows for the recovery of the lactam from the said reaction mixture without formation of by-products and with substantially reduced losses of ammonia by combustion of ammonia.

The process according to the invention for recovering ε-caprolactam from a reaction mixture of ε-caprolactam and sulfuric acid, in which all or part of the sulfuric acid is bound as the ammonium salt to form an aqueous solution or a melt containing the sulfuric acid bound as the ammonium salt, comprises contacting the reaction mixture of ε-caprolactam with a gas containing ammonia and sulfur dioxide, thereby binding the ammonia to the sulfuric acid and discharging the sulfur dioxide as a gas; separating the lactam from the aqueous solution or the melt; and decomposing the ammonium salt in this aqueous solution or melt to form a gaseous mixture containing ammonia and sulfur dioxide.

The sulfur dioxide which is discharged can be converted into sulfuric acid or oleum in a known way, after which this sulfuric acid or oleum can be used in the preparation of the starting reaction mixture.

As a result of the step of contacting the reaction mixture with $NH_3$ and $SO_2$, the ammonium salt formed from sulfuric acid may be, e.g., ammonium sulfate, tri-ammonium hydrogen sulfate and ammonium hydrogen sulfate.

These ammonium salts of sulfuric acid may be decomposed into ammonia and sulfur dioxide by various methods. The ammonium salt may be made to react with a reducing agent, such as, e.g., sulfur and carbon monoxide, at a temperature of 150°–400° C. as disclosed in U.S. Pat. No. 3,810,968 which is hereby relied upon and incorporated by reference. It is also possible to use carbon as the reducing agent at a temperature of 370°–390° C. as disclosed in U.S. Pat. No. 3,275,407 which is relied upon and incorporated by reference, or to use the combustion products of an oil or gas burner at a temperature of 400°–600° C. as disclosed in British patent specification No. 1,014,945 which is relied upon and incorporated by reference.

The hot gases obtained in the decomposition can very suitably be used for preheating the aqueous solution or melt containing the sulfuric acid bound as the ammonium salt.

The neutralization of the sulfuric acid in the reaction mixture to, e.g., ammonium hydrogen sulfate can be effected by passing the gas mixture containing the ammonia and sulfur dioxide into a column through which the reaction mixture is pumped in countercurrent relation to the gas mixture; the heat of neutralization is removed by way of a cooler. Use may also be made of other methods that are known in themselves. When the sulfuric acid is neutralized to ammonium sulfate, the neutralizing method described, e.g., in U.S. Pat. No. 3,907,781, which is incorporated herein by reference, may be employed.

The relative amounts of ammonia and sulfur dioxide in the gaseous mixture are not critical. The amount of ammonia present is effective to neutralize at least 25% of said sulfuric acid to the monoammonium salt of sulfuric acid. The amount of ammonia can range from a 0.25:1 molar ratio (based on moles of sulfuric acid) up to 2:1. The amount of sulfur dioxide in the gaseous mixture obtained in the decomposition is effective to 30 vol.%.

The invention will be illustrated by the Drawings and the Examples.

DESCRIPTION OF THE DRAWINGS

In FIG. 1, A denotes a rearrangement reactor, B a neutralizing device, C an extracting device for extracting the resulting lactam, D a device for the decomposition of ammonium hydrogen sulfate and/or ammonium sulfate, and E an installation for the preparation of sulfuric acid or oleum. The neutralizing device B may consist of the usual apparatus for the absorption of gases, e.g., plate column provided with a cooling jacket through which the rearrangement mixture to be neutralized is recycled by means of a pump. Cyclohexanone oxime is fed through conduit 1 to rearrangement reactor A, which is also fed with oleum through conduit 10. The resulting mixture of lactam and sulfuric acid flows through conduit 2 to neutralizing device B, which is also fed, through conduit 8, with the gas containing ammonia and sulfur dioxide and formed in the decomposition of the ammonium hydrogen sulfate. Optionally, additional ammonia may be fed in through conduit 3. The neutralized mixture flows through conduit 4 to the extracting device C, where the lactam is extracted with organic solvent (organic solvents which may be used include chloroform, 1,2-dichloroethane and 1,1,2,2-tetrachloroethane) supplied through conduit 5 and is discharged as a solution of lactam in the solvent through conduit 6 to a device (not shown) for the recovery of lactam. The aqueous phase from extracting device C is passed through conduit 7 to device D for the decomposition of ammonium hydrogen sulfate, the decomposition being effected by means of a reducing agent, e.g., coke, supplied through conduit 13.

Figure 1:
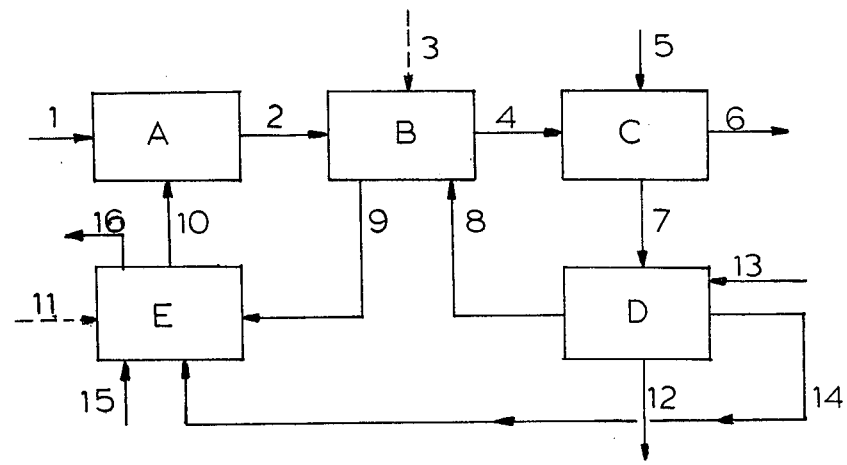
FIG. 1 shows the preparation of ε-caprolactam in which the rearrangement mixture is neutralized to ammonium hydrogen sulfate.

The resulting gaseous mixture containing substantially $NH_3$ and $SO_2$ is passed through conduit 8 to neutralizing device B, where the $NH_3$ is used to neutralize the sulfuric acid from the mixture of lactam and sulfuric acid to form ammonium hydrogen sulfate. The $SO_2$ escapes and is passed through conduit 9 to the installation E for the preparation of oleum, which is also fed with oxygen through conduit 15, with water vapor formed by evaporation of the solution fed in through conduit 7 through conduit 14, and, if necessary, with liquid sulfur through conduit 11. The residual liquid components in device D are vented from the system through conduit 12 and a gas containing mainly carbon dioxide is removed through conduit 16. This carbon dioxide is formed by oxidation of the carbon monoxide formed in the reduction of hydrogen sulfate in the oleum installation E.

Figure 2:
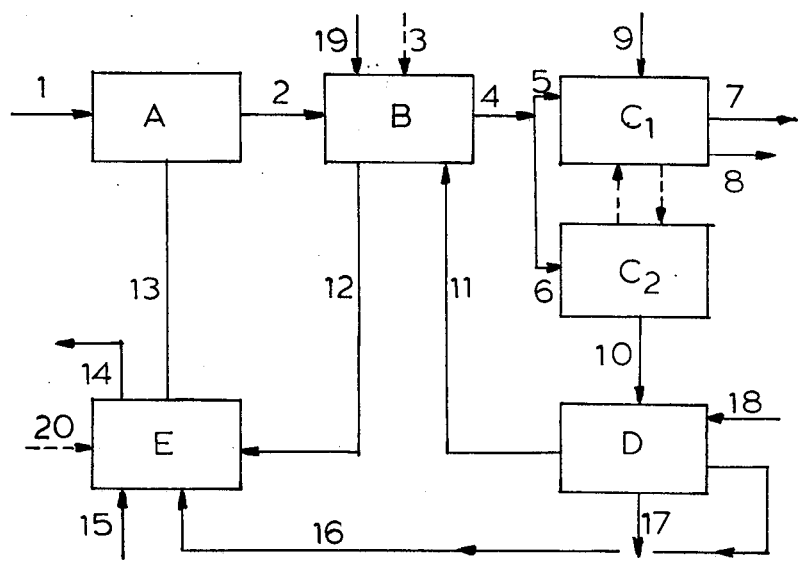
FIG. 2 shows lactam preparation where the sulfuric acid is neutralized to ammonium sulfate.

In FIG. 2, which shows a lactam preparation in which the rearrangement mixture is neutralized to ammonium sulfate, the letters A, B, D, and E denote similar devices to those in FIG. 1. The flows 1, 2, 3 and 4 are the same as those mentioned in FIG. 1. Neutralizing device B is fed with an amount of water through conduit 19 to keep the water concentration at the desired level. The extraction of lactam is effected in two extracting devices C1 and C2 that are connected by two conduits. After the neutralized reaction mixture supplied through conduit 4 has been separated into two liquid layers, the organic layer is passed through conduit 5 to extracting device C1 and the aqueous layer containing ammonium sulfate is passed through conduit 6 to extracting device C2. The organic solvent is supplied through conduit 9 and the lactam-laden solvent is discharged through conduit 7. Tar and water can be vented through conduit 8. The aqueous ammonium sulfate layer is passed through conduit 10 to decomposition device D, where it is decomposed by means of coke supplied through feed 18. The resulting gases containing ammonia and sulfur dioxide are passed through conduit 11 to neutralizing device B and the sulfur dioxide escaping from this device is passed through conduit 12 to installation E for the preparation of oleum, which is fed with water vapor formed in the decomposition of ammonium sulfate through conduit 16, with oxygen through conduit 15, and, if so required, with sulfur through conduit 20. The residual liquid components in device D are drained from the system through conduit 17 and a gas containing mainly carbon dioxide is removed through conduit 14.

In the following Examples it is assumed that the efficiency of the decomposition reaction amounts to 100%. In practice, of course, this is not the case and losses of $NH_3$ and $SO_2$ must be replenished.

EXAMPLE I

According to the diagram of FIG. 1, 100 kg of ε-caprolactam are prepared while 3 kg of cyclohexanone oxime are fed to the rearrangement reactor per hour. The neutralization is effected at atmospheric pressure and at a temperature of about 40° C. The resulting ε-caprolactam is extracted with chloroform. The ammonium hydrogen sulfate formed in the neutralization is decomposed by means of coke according to the gross equation:

$$NH_4HSO_4 + C \rightarrow NH_3 + SO_2 + H_2O + CO$$

The composition of the various material flows (in kg) is shown in Table 1.

Table 1

| Flow | Oxime | Lactam | $H_2SO_4$ | $NH_4HSO_4$ | $H_2O$ | $SO_2$ | $NH_3$ | CO | $CO_2$ | $O_2$ | $CHCl_3$ | C | S | Total |
|---|---|---|---|---|---|---|---|---|---|---|---|---|---|---|
| 1 | 100 | | | | | | | | | | | | | 100 |
| 2 | | 100 | 130 | | | | | | | | | | | 230 |
| 3 | | | | | | | | | | | | | | |
| 4 | | 100 | | 152.5 | 152.5 | | | | | | | | | 405 |
| 5 | | | | | | | | | | | 300 | | | 300 |
| 6 | | 100 | | | | | | | | | 300 | | | 400 |
| 7 | | | | 152.5 | 152.5 | | | | | | | | | 305 |
| 8 | | | | | 152.5 | 85 | 22.5 | 37 | | | | | | 122 |
| 9 | | | | | | 85 | | 37 | | | | | | |
| 10 | | | 130 | | | | | | | | | | | 130 |
| 11 | | | | | | | | | | | | | | |
| 12 | | | | | | | | | | | | | | |
| 13 | | | | | | | | | | | | 16 | | 16 |
| 14 | | | | | 24 | | | | | | | | | 24 |

EXAMPLE II

According to the diagram of FIG. 2, 100 kg of ε-caprolactam are prepared while 3 kg of cyclohexanone oxime were fed to the rearrangement reactor per hour. The neutralization is effected at atmospheric pressure and at about 50° C. The resulting ε-caprolactam is extracted with benzene. The ammonium sulfate formed in the neutralization is decomposed by means of coke according to the gross equation:

$$(NH_4)_2SO_4 + C \rightarrow 2\ NH_3 + SO_2 + H_2O + CO$$

The composition of the various material flows (in kg) is given in Table 2.

Table 1-continued

| Flow | Oxime | Lactam | $H_2SO_4$ | $NH_4HSO_4$ | $H_2O$ | $SO_2$ | $NH_3$ | CO | $CO_2$ | $O_2$ | $CHCl_3$ | C | S | Total |
|---|---|---|---|---|---|---|---|---|---|---|---|---|---|---|
| 15 | | | | | | | | | | 42 | | | | 42 |
| 16 | | | | | | | | | 58 | | | | | 58 |

Table 2

| | Oxime | Lactam | $H_2SO_4$ | $(NH_4)_2SO_4$ | $H_2O$ | $SO_2$ | $NH_3$ | CO | $CO_2$ | $O_2$ | Benzene | C | S | Total |
|---|---|---|---|---|---|---|---|---|---|---|---|---|---|---|
| 1 | 100 | | | | | | | | | | | | | |
| 2 | | 100 | 130 | | | | | | | | | | | 230 |
| 3 | | | | | | | | | | | | | | |
| 4 | | 100 | | 175 | 306 | | | | | | | | | 581 |
| 5 | | 100 | | | 43 | | | | | | | | | 143 |
| 6 | | | | 175 | 263 | | | | | | | | | 438 |
| 7 | | 100 | | | | | | | | | 400 | | | 500 |
| 8 | | | | | 43 | | | | | | | | | 43 |
| 9 | | | | | | | | | | | 400 | | | 400 |
| 10 | | | | 175 | 263 | | | | | | | | | 438 |
| 11 | | | | | 263 | 85 | 43 | 37 | | | | | | 430 |
| 12 | | | | | | 85 | | 37 | | | | | | 122 |
| 13 | | | 130 | | | | | | | | | | | 130 |
| 14 | | | | | | | | | 58 | | | | | 58 |
| 15 | | | | | | | | | | 42 | | | | 42 |
| 16 | | | | | 24 | | | | | | | | | 24 |
| 17 | | | | | | | | | | | | | | |
| 18 | | | | | | | | | | | | | 16 | 16 |
| 19 | | | | | 43 | | | | | | | | | 43 |
| 20 | | | | | | | | | | | | | | |

What is claimed is:

1. In a process for the recovery of ε-caprolactam from a reaction mixture containing ε-caprolactam and sulfuric acid in which at least a part of said sulfuric acid is treated with a source of ammonia to convert said sulfuric acid to an ammonium salt thereof in a melt or an aqueous solution, the improvement comprising (1) contacting said sulfuric acid with a gaseous mixture of ammonia and sulfur dioxide to form said salt; and discharging sulfur dioxide as a gas; (2) separating said lactam from the melt or aqueous solution of said salt; and (3) converting said salt to ammonia and sulfur dioxide.

2. The process of claim 1, wherein the sulfur dioxide which is discharged in (1) is reacted with water and oxygen to form sulfuric acid.

3. The process of claim 2, wherein said sulfuric acid is used in the preparation of said reaction mixture.

4. The process of claim 1, wherein said ammonia and sulfur dioxide of (3) is passed into (1).

* * * * *